US 9,644,763 B2

(12) United States Patent
Flucke (10) Patent No.: US 9,644,763 B2
(45) Date of Patent: May 9, 2017

(54) HOLDING DEVICE

(71) Applicant: Eppendorf AG, Hamburg (DE)

(72) Inventor: Christian Flucke, Hamburg (DE)

(73) Assignee: EPPENDORF AG, Hamburg (DE)

( * ) Notice: Subject to any disclaimer, the term of this patent is extended or adjusted under 35 U.S.C. 154(b) by 0 days.

(21) Appl. No.: 13/938,148

(22) Filed: Jul. 9, 2013

(65) Prior Publication Data

US 2014/0014786 A1   Jan. 16, 2014

Related U.S. Application Data

(60) Provisional application No. 61/669,599, filed on Jul. 9, 2012.

(30) Foreign Application Priority Data

Jul. 9, 2012  (DE) .................. 10 2012 013 465

(51) Int. Cl.
*A47G 1/10* (2006.01)
*F16L 3/02* (2006.01)
(Continued)

(52) U.S. Cl.
CPC . *F16L 3/02* (2013.01); *B25J 7/00* (2013.01); *F16M 11/041* (2013.01);
(Continued)

(58) Field of Classification Search
CPC  G02B 21/32; B25J 7/00; F16M 13/00; F16M 13/02; F16M 13/022; G01N 23/2204
(Continued)

(56) References Cited

U.S. PATENT DOCUMENTS 3,057,230 A * 10/1962 Elledge .......................... 408/90
3,238,351 A *  3/1966 Hill ............................ 219/86.61
(Continued)

FOREIGN PATENT DOCUMENTS

CN     101182900 A    9/2010
CN     201795241 U    4/2011
(Continued)

*Primary Examiner* — Brian Mattei
*Assistant Examiner* — Taylor Morris
(74) *Attorney, Agent, or Firm* — Todd A. Lorenz (57) ABSTRACT

The invention relates to a holding device (1) for holding an object (2) extending along an axis, in particular for holding the capillary holder (2) of a micromanipulator, with a main body (3, 4) having a bearing element (4) which runs parallel to a bearing axis and on which the object (2) can be mounted in an axis-parallel position in which the axis of the object and the bearing axis (A) of the bearing element run parallel, a fastening mechanism (4, 5, 6, 7, 8) which is designed in such a way and can be optionally set by the user in at least a first or a second arrangement in such a way that, in the first arrangement of the fastening mechanism, the object (2) is secured with a force fit on the bearing element (4) in the axis-parallel position (A) by a first force, such that it is movable by a hand of a user in the axis-parallel position, and in such a way that, in the second arrangement of the fastening mechanism, the object (2) is fixed on the bearing element in the axis-parallel position (A), wherein the holding device (1) is designed such that the object (2), at least in a third arrangement of the fastening mechanism, can be inserted into and removed from the holding device (1) by a movement directed perpendicularly with respect to the bearing axis (A).

5 Claims, 2 Drawing Sheets

(51) Int. Cl.

| | | |
|---|---|---|
| *B25J 7/00* | (2006.01) | |
| *F16M 11/04* | (2006.01) | |
| *F16M 11/08* | (2006.01) | |
| *F16L 3/08* | (2006.01) | |
| *F16L 3/12* | (2006.01) | |
| *A47G 29/00* | (2006.01) | |
| *F16M 11/00* | (2006.01) | |
| *F16M 13/02* | (2006.01) | |
| *F16M 13/00* | (2006.01) | |
| *G02B 21/32* | (2006.01) | |
| *G01N 23/22* | (2006.01) | |

(52) U.S. Cl.
CPC ........... *F16M 11/043* (2013.01); *F16M 11/08* (2013.01); *F16M 13/00* (2013.01); *F16M 13/02* (2013.01); *F16M 13/022* (2013.01); *F16M 2200/022* (2013.01); *F16M 2200/027* (2013.01); *G01N 23/2204* (2013.01); *G02B 21/32* (2013.01)

(58) Field of Classification Search
USPC ......... 248/65, 70, 72, 74.1, 74.2, 74.4, 74.5, 248/117.7, 316.3, 316.6, 689; 29/559; 451/248; 396/428
See application file for complete search history.

(56) References Cited

U.S. PATENT DOCUMENTS

| | | | | |
|---|---|---|---|---|
| 4,332,363 A | | 6/1982 | Ware | |
| 4,626,906 A | * | 12/1986 | Ensor | ............................... 348/79 |
| 4,995,539 A | * | 2/1991 | Richard | ............................ 225/2 |
| 5,163,728 A | * | 11/1992 | Miller et al. | ................. 294/99.1 |
| 5,271,588 A | * | 12/1993 | Doyle | ........................ 248/68.1 |
| 5,476,241 A | | 12/1995 | Helman | |
| 5,671,523 A | * | 9/1997 | Juchinewicz | ................... 29/559 |
| 5,741,252 A | * | 4/1998 | Mazzio | .............. A61B 17/6483 |
| | | | | 606/54 |
| 5,752,807 A | * | 5/1998 | Erbes | ............................... 417/63 |
| 6,415,679 B1 | * | 7/2002 | Chiodo | ...................... 74/490.15 |
| 6,584,269 B1 | * | 6/2003 | Mitchell et al. | .............. 385/136 |
| 7,241,060 B2 | * | 7/2007 | Mootz et al. | ................. 396/421 |
| 7,798,459 B2 | * | 9/2010 | Dickson | ...................... 248/316.3 |
| 2005/0056740 A1 | | 3/2005 | Chuang | |
| 2006/0177215 A1 | | 8/2006 | Johnson | |
| 2010/0031519 A1 | * | 2/2010 | Guiney et al. | ............... 33/27.01 |
| 2011/0147550 A1 | * | 6/2011 | Wendler et al. | ........... 248/218.4 |

FOREIGN PATENT DOCUMENTS

| | | |
|---|---|---|
| CN | 202025178 U | 11/2011 |
| DE | 34 03 898 A1 | 8/1985 |
| DE | 42 24 002 A1 | 1/1994 |
| DE | 202 10 101 U1 | 9/2002 |
| DE | 20 2008 008 224 U1 | 11/2008 |
| FR | 692 625 A | 11/1930 |
| JP | 2001 330781 A | 11/2001 |
| WO | PCT/EP2013/002020 | 7/2003 |
| WO | WO 2014/009006 A1 | 1/2014 |

* cited by examiner

HOLDING DEVICE

The invention relates to a holding device for holding an object extending along an axis, in particular for holding the capillary holder of a micromanipulator.

Such holding devices are used in laboratories for the purpose of arranging objects in a precisely predetermined or precisely definable position and for holding them there. In the use of such a holding device on a micropositioning device or a micromanipulator device, or as a component part of such devices, only the very slightest tolerances are allowed when micropositioning is performed. Micromanipulation can entail the manipulation of man-made items, e.g. microsystems or nanosystems and components thereof. It can concern in particular the manipulation of biological items, e.g. living cells. Both areas of use require a high degree of reliability in the positioning of the manipulation tools, e.g. capillaries, probes or electrodes.

Holding devices of the present kind are particularly beneficial for use in cell biology and molecular biology workstations, where a user has to precisely position capillary holders or other objects extending along an axis. At such workstations, for example, methods such as intracytoplasmic sperm injection (ICSI) and the transfer of embryonic stem cells (ES cells) in blastocysts are performed, which require precise control of the position and movement of the used tool within a very confined space. Such workstations often have several appliances and apparatuses and their modules, which permit a large number of settings and functions. These appliances and apparatuses, mounted substantially around and on the microscope, are all spatially close to one another. All measures taken within this workstation to reduce the effort on the part of the user increase the efficiency and heighten the productivity and ergonomics at such a workstation.

In this connection, it is particularly desirable to provide a holding device that is efficient and comfortable to operate. In particular, it is desirable that such a holding device can be safely operated using one hand. This allows the user to use one hand to operate the holding device while at the same time using the other hand to operate another component of the workstation, for example a microscope. In performing cell manipulations, a typical procedure involves moving the tool, e.g. the capillary in a capillary holder, initially over a range of several centimeters to a point near a container with the cell in nutrient solution, which is generally done manually. Only then, by means of an electrical micromanipulator, is the capillary guided with a precision of some tens of nanometers to the cell and/or driven into the cell. In the context of this invention, it was found that the method can in many cases be carried out more efficiently, the nearer the user can move the capillary manually to the target point. To do so, the user observes the movement of the capillary relative to the target point under the microscope and, if necessary, uses one hand to change the resolution of the microscope or to adjust the focus. In this situation, comfortable operation of the holding device is important in order to be able to coordinate the work sequences.

The problem addressed by the invention is that of making available a holding device by means of which an object extending along an axis is reliably held and which is comfortable to operate.

The invention solves this problem in particular by means of the holding device according to Claim 1. Preferred embodiments are the subject matter in particular of the dependent claims.

An advantage of the invention is that an easy movement of the object arranged in the first arrangement on the holding device is possible. This is because the fastening mechanism is designed such that, in the first arrangement, the object is firstly held in the actual position by the first force, when it is not moved by the user, and secondly can be moved in this position by the user in the axis-parallel position, in particular without affecting the position of the bearing element. By maintaining the axis-parallel position also during the manual movement of the object held in the first arrangement, a high degree of productivity is permitted since, after the movement, the user does not have to readjust the object in the direction perpendicular to the bearing axis. In particular, the holding device can thus be operated using one hand.

Moreover, the object can be easily fixed in the desired target position. In addition, the user can optionally set the first arrangement and the second arrangement of the fastening mechanism. In this way, the holding device can be operated reliably and comfortably. An efficient and ergonomic work sequence is achieved in which, firstly, a manual movement of the capillary holder can be effected by hand exclusively along its axis, without radial torque, and, secondly, the capillary holder can be fixed in the desired end position, in particular can be fixed with precision in a continuously axially variable end position.

The holding device is preferably a mechanical device without electrically operated components. It can thus be used flexibly. However, it can also have electrically operated components, which makes it necessary to provide a source of electrical power, in particular a battery or a power pack, and/or a cable mechanism for supplying energy and/or for electrical control.

The holding device is preferably compact and is suitable for arrangement, in particular for mounting, on a laboratory object. The laboratory object is preferably a microscope, in particular an optical microscope. Between laboratory object and holding device, a securing device and/or support device is preferably provided for the holding device, e.g. a movement device on which the holding device is movably mounted. The laboratory object can also be another laboratory appliance, laboratory installation or machine. The laboratory object can also be a bench, preferably a laboratory workbench or a desk.

The mass of the holding device is preferably less than 500 grams, preferably less than 250 grams, preferably less than 150 grams, preferably less than 100 grams. The volume of the holding device is preferably less than 600 $cm^3$, preferably less than 300 $cm^3$, preferably less than 150 $cm^3$, wherein the volume is assumed as the smallest cube that the holding device can occupy completely. By these measures, the holding device can be operated easily and efficiently and, in particular as an auxiliary mechanism of a laboratory workstation, fits into the surroundings without taking up much space.

The main body is a component on which the bearing element is secured movably or immovably. The bearing element can also be designed in one piece with the main body, e.g. as a component that is cast or milled in one piece. The main body preferably has a securing means with which it can be secured on a laboratory object, e.g. on the carriage of a movement mechanism. The securing means can be a section of the main body serving for securing purposes, can have at least one recess or opening, e.g. with internal thread, at least one projecting section or a roughened area of the main body, or can be a separate component which is mounted on the main body, e.g. a bolt, pin, e.g. with thread, a shaft, etc.

The main body preferably has a support element, on which the bearing element is secured so as to be rotatable about at least one axis R, preferably to be rotatable about precisely one axis. The main body can have an adjusting mechanism for adjusting the relative rotation of support element and bearing element about a rotation axis R. The adjusting mechanism preferably has an axle element, e.g. a pin or bolt, by means of which the support element and the rotation element are rotatable about the axis R of the axle element. The adjusting mechanism can also have a fixing mechanism, in particular a clamping mechanism, such that the bearing element rotated with respect to the support element can be fixed in the desired, preferably continuously variable relative position and can be released again. Alternatively, another fixing mechanism can be provided for defining the rotation angle. The fixing mechanism preferably has an actuating element, e.g. a rotary wheel, with which the user can effect the fixing/release. In addition or alternatively, an angle adjuster can also be provided by which the at least one rotation angle is changed, in particular mechanically or electromechanically. The angle adjuster can have a mechanical part with, for example, a toothed gear, friction gear or belt gear.

The object which extends along an axis, and which can be held by means of the holding device, can in particular be an elongate object with a length L, which in at least one direction, preferably in all directions, perpendicularly away from the axis, designated as radially, has a smaller size S than in the axial direction, wherein the size S can be in particular the diameter S=D or an edge length S=a, which runs perpendicular to the axis A and does not cross this. Preferably, L>c*D, where c can be a number in the range of 2 to 100, for example. At least in some areas in the axial direction, or substantially along its entire length, the object preferably has a constant cross section perpendicular to the axis. The object is preferably cylindrical, in particular in the form of a hollow cylinder, at least in the section in which it is held, or preferably along the greater part of its length L. However, it can also have a differently shaped cross section, in particular rectangular, quadratic, square, polygonal or ellipsoid.

The object can be substantially non-deformable, e.g. made of metal or plastics, or it can be deformable, e.g. made of elastic material.

The object is preferably a tool holder, in particular a capillary holder of metal or plastics, of which one end can have a securing section for securing a tool, in particular a capillary, in the axial direction, and/or of which the other end can have a connecting section for a tube. The tool holder is preferably a micromanipulator which is designed for moving the tool, for example by having a piezoelectric element. The micromanipulator is preferably a PiezoXpert® actuator, which is commercially available with the PiezoXpert® system from Eppendorf AG, Hamburg, Germany.

The fastening mechanism is designed in such a way, and can be optionally set by the user in at least a first or a second arrangement in such a way, that, in the first arrangement of the fastening mechanism, the object is secured with a force fit on the bearing element in the axis-parallel position, such that it is held on the bearing element in the axis-parallel position by a first force F1 directed parallel to the axis, wherein the object is movable in this axis-parallel position, particularly by a hand of a user, when the first force F1 is overcome. The first force F1 directed parallel to the axis corresponds to the breakaway force that the user has to apply in order to release the force-fit connection. This force corresponds here to the static friction force $F1_R$, which effects the force-fit connection.

Force fit means that a normal force is exerted on the surfaces to be connected to each other, such that their mutual movement is prevented as long as the counterforce $F_R$, here $F1_R$ and $F2_R$, effected by the static friction is not exceeded. The term force fit is used synonymously with the term friction fit. The surfaces attaching by friction are in the present case preferably surfaces of the object and of the bearing element, in particular also of a pressure element.

In the second arrangement of the fastening mechanism, the object is fixed in the axis-parallel position on the bearing element. This is preferably achieved by a force-fit connection, wherein the object is held in the axis-parallel position by a second force F2 directed parallel to the axis, which second force F2 is greater than the first force, and wherein, at this second force F2, the secured object cannot be moved in particular by a hand of a user in the axis-parallel position. In this second arrangement of the securing mechanism, the force-fit connection of object and holding device is preferably achieved via the same connecting elements that also generate the first force. F2 is greater than F1, preferably at least 25%, at least 50% or at least 100% greater. F1 is preferably between 0.3 N and 15 N, preferably between 0.5 Newton (N) and 10 N, particularly preferably between 0.5 N and 5.0 N. The lower limit for F1 should be chosen to be at least such that the held object does not come loose from the holding device by gravity. The normal force with which the holding device presses the object perpendicularly onto the bearing element is approximately 2.0 N to 10.0 N, when the first force is between 0.5 N and 5.0 N. Here, fixed means that the object fixed in the holding device cannot be released by a user with one hand when the force exerted for movement parallel to the axis is less than this second force. F2 is preferably greater than 25 N, preferably greater than 50 N, preferably greater than 100 N. F2 is preferably less than 200 N, so as not to damage the holding device or the object. The fixing, in the second arrangement of the securing mechanism, can also be achieved by the fact that, in the second arrangement, a connection of the object to the holding device is obtained at least partially or completely by a form fit.

In the case of all the range limits stated in this description for parameters, in particular F1 and F2, provision can preferably be made that the range limit should also be included in the stated range if this is not already so described, e.g. 0.5N<=F1<=5.0 N.

The force F1 and/or F2 can in particular be measured by a force sensor which measures the tensile force in the direction parallel to the axis. Alternatively, the force F1 and/or F2 can in particular be measured by a force sensor which measures the pressure force in the direction parallel to the axis. The pressure sensor can be a spring balance with which a tensile force or pressure force can be measured.

The holding device is preferably designed such that the object, at least in a third arrangement of the fastening mechanism, can be inserted into the holding device and in particular can be removed therefrom by a movement directed perpendicularly with respect to the bearing axis A. This movement can also have components parallel to the bearing axis A. This design permits comfortable operation of the holding device even when it is accessible only from one side, e.g. because the side opposite this side is blocked by components, e.g. by a support device for supporting the holding device or by a securing mechanism. However, it is also possible and preferable that the object, at least in a third arrangement of the fastening mechanism, can be inserted into the holding device and removed therefrom by a movement directed parallel to the bearing axis A, particularly when, for this movement, only the axis-parallel area is available that is located in the continuation of the axis-parallel position.

The holding device is designed such that the object, at least in a third arrangement of the fastening mechanism, can be inserted into the holding device and can be removed therefrom by a movement directed perpendicularly with respect to the bearing axis. It is also possible and preferable that the object, in the first arrangement of the fastening mechanism, can be inserted into the holding device and removed therefrom by a movement directed perpendicularly with respect to the bearing axis. In this case, during the removal, the user overcomes in particular the normal force with which the holding device presses the object perpendicularly onto the bearing element. The handling of the holding device is thus easy and comfortable, since the object does not in particular have to be engaged in the axial direction through an axially directed opening, for which provision may however also be made in an alternative embodiment. The holding device preferably has a substantially U-shaped or claw-shaped cross section perpendicular to the bearing axis, such that the object can be inserted in a direction to the bearing axis, in particular in a radial direction, even if it always remains arranged parallel to the bearing axis during insertion.

The fastening mechanism preferably has a pressure element mounted movably on the holding mechanism, wherein, in the first arrangement and second arrangement of the fastening mechanism, the object is pressed against the bearing element by the pressure element, resulting in a force-fit fastening of the fastening mechanism. The pressure element is preferably a plate-shaped element, which preferably has one or more openings or recesses for receiving a pin or a threaded bolt.

The fastening mechanism is preferably designed as a clamping mechanism in order to hold the object preferably in manually continuously variable axial positions. The fastening mechanism preferably has a thread mechanism or an eccentric mechanism. The thread mechanism can be provided in the form of a rotary wheel element with a threaded section, wherein the threaded section can be a cylindrical recess with internal thread or a bolt section with external thread. The thread is preferably a single-start or multi-start thread, preferably a spiral thread. However, the fastening mechanism can also have a bayonet connection, with at least one bayonet groove for the constrained guiding of at least one bayonet projection, these being able to be arranged matching each other on the rotary wheel and on a connecting element between bearing element and rotary wheel. By manual rotation of the rotary wheel element, the first and/or second force can be applied. The eccentric mechanism can have an eccentric element, e.g. an eccentric disc, by whose manual rotation the first and/or second force can be applied.

The rotary wheel element preferably has a contact section for making contact with the object or the pressure element via a contact face, in order to transfer the first and/or second force via this contact face. Preferably, the rotary wheel has a first receiving space in which an internal thread is arranged, which in particular is assigned to the thread mechanism. The first receiving space preferably serves to receive a connecting element between bearing element and rotary wheel, preferably a threaded pin which at one end can be connected, e.g. by means of a thread, to the bearing element and at the other end has the external thread for the internal thread of the rotary wheel. Preferably, the rotary wheel has at least one second receiving space to receive the spring element of a spring mechanism. A receiving space is preferably a cylindrical recess or opening which is provided in the rotary wheel, coaxially with respect to the rotation axis of the rotary wheel, preferably in the side that has this contact face. The first and second receiving spaces can be designed coaxially with and merging into one another, in particular rotationally symmetrically with respect to the rotation axis. The contact face is also preferably rotationally symmetrical with respect to the rotation axis. An axially directed force is thus brought about, as a result of which the application of force via the contact face is uniform. However, the first and second receiving spaces can also be separated by a dividing wall.

The spring element is preferably a compression spring, preferably a helical spring, although it can also be another element with dimensional elasticity and/or material elasticity.

In the first arrangement, the pressure element is preferably pressed resiliently against the object by the spring mechanism, such that the pressure element remains deflectable counter to the action of the spring force.

Preferably, the fastening mechanism is also designed such that the pressure element, in the second arrangement, is pressed non-resiliently against the object, such that the pressure element is not deflectable counter to the direction of the spring force. It is also possible and preferable that the pressure element, in the first arrangement, is pressed resiliently against the object by the first force F1 and, in the second arrangement, is pressed resiliently against the object by a second force F2, where F1<F2.

The fastening mechanism preferably has an actuating element with which the user can optionally set the first or the second arrangement of the fastening mechanism, wherein the actuating element is a rotary knob rotatable about a rotary-knob axis. The rotary knob is preferably mounted on the bearing element and serves in particular as abutment for the spring mechanism which, in the first arrangement of the fastening mechanism, transfers a first force to the pressure element and therefore to the object, wherein preferably in the second arrangement of the fastening mechanism a contact section of the rotary knob additionally contacts the pressure element and presses against the pressure element such that, by means of this contact section and the spring mechanism, the rotary knob transfers the second force F2 to the pressure element, which second force F2 is greater than the first force F1 and fixes the object on the bearing element.

The fastening mechanism is preferably designed as a quick-action clamping mechanism, with the user being able to effect the change between the first and second arrangements by turning the rotary knob about the rotary-knob axis by a predetermined rotation angle $\alpha_1$, where $\alpha$ is chosen from the group of respectively preferred angle ranges $\{(5°<=\alpha_1<=360°); (5°<=\alpha_1<=270°); (5°<=\alpha_1<=45°); (5°<=\alpha_1<=90°); (90°<=\alpha_1<=135°); (135°<=\alpha_1<=165°); (145°<=\alpha_1<=195°); (165°<=\alpha_1<=195°)\}$. Proceeding from an angle setting of the second arrangement of the fastening mechanism, to which the value $\alpha=0$ degree is assigned, provision is preferably made that the stated change between first arrangement and second arrangement takes place by turning the rotary knob in the range $0.5°<=\alpha_1<=90°$, or one of the ranges mentioned above. The user can preferably effect the change by turning the rotary knob to the setting $\alpha_1$, in particular with less than a half turn of the rotary knob, which permits a rapid work sequence. The holding device is preferably designed such that, proceeding from the second arrangement of the fastening mechanism, a third arrangement can be produced in which the object is removable, with the rotary knob being turned onwards to an angle $\alpha_2$ which, proceeding from said zero setting, preferably lies between 180° and 360°.

The fastening mechanism can also be designed as a magnetic clamping mechanism in which the force for clamping is effected magnetically. The magnetic force acting between a magnet element and a magnetic element is in particular dependent on their distance and on the nature of the material separating them, particularly its magnetic permeability. In order to use the magnetic force as variable clamping force, a spacer mechanism is therefore preferably provided with which the distance between the magnet element and the magnetic element can be varied. The magnet element can be the bearing element, for example, and the magnetic element can be the pressure element, or the rotary wheel, which then preferably contacts the object to be held in the first and second arrangements. The rotary wheel can then be a component part of the spacer mechanism, such that turning it also changes the distance. The first force is then generated at a greater distance than the second force. The spacer mechanism can have a thread mechanism in order to continuously vary the distance. It is also possible to use two magnet elements which hold a magnetic or magnetizable element (e.g. the capillary holder). These two first magnet elements can then be moved relative to each other on the correspondingly designed holding device such that their fields add to each other, as a result of which the second arrangement is achieved, or cancel each other completely (e.g. in the third arrangement) or partially (e.g. in the first arrangement).

If the object to be held is magnetic in the holding area or has a magnet, this permits other design possibilities than if it is non-magnetic. In this case, the bearing element can be a permanent magnet or at least have a magnet element which has a permanent magnet. The holding magnetic element or the element having a magnet can then be arranged on the bearing element such that the object is not pressed against the bearing element but instead drawn against it, e.g. on a side of the bearing element lying opposite the contact face of the bearing element for contact with the object. In this case, the spacer mechanism is designed such that the distance of the holding element from the bearing element is changed.

The bearing element, preferably also the pressure element, is made of a substantially non-deformable material, preferably a metal or plastic or ceramic, preferably at least in those sections where it contacts the object in the first and second arrangements of the fastening mechanism. This permits precise positioning of the object when it is held between these sections. The material can be magnetic, in particular ferromagnetic, or can be a permanent magnet.

The bearing element is preferably designed for partially also form-fit connection of the object to the holding device, preferably in the first and second arrangements. The bearing element is preferably designed in such a way that an individual contact point of the pressure element with a cylindrical object suffices to effect the first arrangement and second arrangement of the fastening mechanism. That is to say, the bearing element is preferably designed such that it supports the cylindrical object at at least three points, preferably four points. The bearing element preferably has an insert groove or insert channel or several groove sections or claw sections by which the object can be held in an axially fixed manner. The bearing axis then runs through the receiving area of the groove or channel parallel to the groove direction.

Through the positioning by means of an insert groove made of non-elastic material, an acoustic signal is generated, namely a click, when the object inserted by the user and made of such a material slides into the clearly defined bearing position formed by the insert groove, particularly if it is pressed into the bearing position by means of the spring force of a spring mechanism. This acoustic feedback likewise permits comfortable operation of the holding device.

The bearing element preferably has an axis-parallel insert groove for insertion of the object, and the pressure element is in this case plate-shaped and has two opposite plate faces, wherein, in the first and second arrangements, a contact area of one plate face contacts the object and presses it against the insert groove.

Further preferred configurations of the operating device according to the invention and of the method according to the invention will become clear from the following description of the illustrative embodiments in connection with the figures and the description thereof. Identical components in the illustrative embodiments are identified principally by identical reference signs unless otherwise stated or unless appears otherwise from the context. In the figures:

Figure 1:
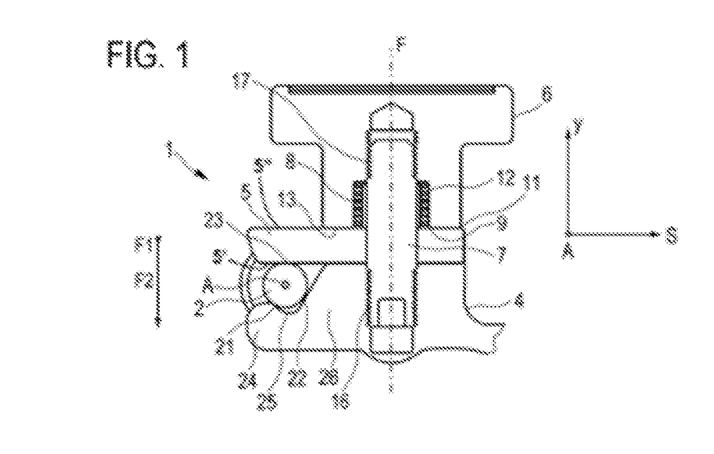
FIG. 1 shows a cross section through a holding device according to an illustrative embodiment of the invention, along the line S shown in FIG. 2.
Figure 2:
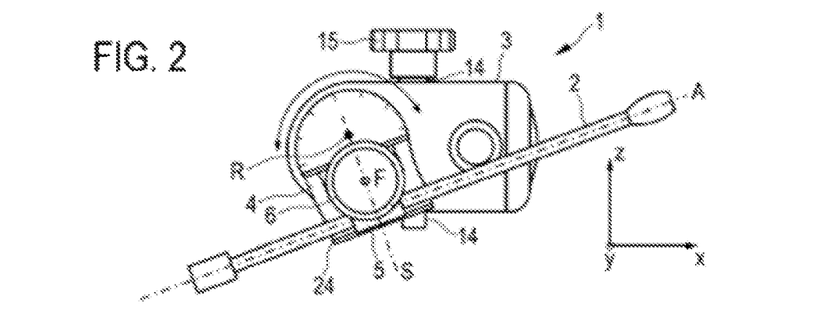
FIG. 2 shows a side view of the holding device from FIG. 1.
Figure 3:
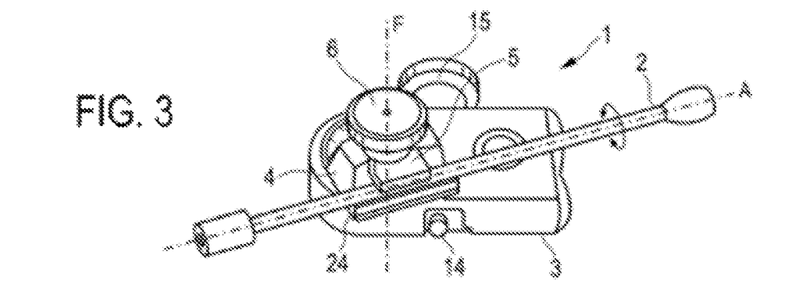
FIG. 3 shows a perspective view of the holding device from FIG. 1.

FIG. 1 shows a cross section through the holding device 1, along the line S shown in FIG. 2. The holding device 1 is a quick-action clamping mechanism for holding an object 2 which extends along an axis and which in the present case is the capillary holder 2 of a micromanipulator (not shown). The holding device 1 has a main body 3, 4 having a bearing element 4 which runs parallel to a bearing axis A and on which the object 2 can be mounted in an axis-parallel position, as is shown, in which the axis of the object and the bearing axis A of the bearing element run in parallel or coincide. Moreover, the main body has a support element 3 (FIG. 2, FIG. 3), on which the bearing element 4 is mounted rotatably.

The bearing element is secured on the support element so as to be rotatable about the axis R. The holding device has an adjusting mechanism 14, 15 for adjusting the relative rotation of support element 3 and bearing element 4. The adjusting mechanism has a shaft 14 by means of which the support element and the rotation element are rotatable about the axis R. Centrally, the shaft 14 has a worm as part of the gear (not shown) and, at the end, has a receiver for the knob 15. The adjusting mechanism is also designed as an angle adjuster, with which the at least one rotation angle can be adjusted via a gearing (not shown) of the holding device. The angle adjuster 14, 15 has, as actuating element, the rotary wheel 15 which can turn about the shaft 14 and with which the user can adjust the rotation angle between support element and bearing element.

The fastening mechanism has the bearing element 4, the pressure plate 5 forming the pressure element, the rotary wheel 6 serving as actuating element, the threaded pin 7, and the helical spring 8 which belongs to the spring mechanism and acts as compression spring.

FIG. 1 shows the second arrangement of the fastening mechanism. The compression spring 8 is arranged in a cylindrical recess 12 of the rotary wheel, which recess 12 is coaxial with respect to the receiver for the threaded pin 7 surrounded coaxially by the compression spring 8. Towards the face of the pressure plate, the compression spring presses uniformly on the pressure plate 5 in the direction of the axis F, wherein F is perpendicular to the bearing axis A, in order to provide the maximum pressing force. Towards the top, in the direction away from the pressure plate, the compression spring is supported on the rotary wheel that serves as abutment. The rotary wheel is connected to the bearing element via the threaded pin 7. The position of the rotary wheel 6 along the axis F changes only through rotation of the rotary wheel, as a result of which the clamping force is continuously variable. Between the lower face 13 of the rotary wheel and the pressure plate 5, a small air gap 11 remains in the first arrangement, specifically to the right of the axis F in the figure, whereas to the left of the axis F the rotary wheel is in contact with the pressure plate and thus transfers a force to the pressure plate, such that the latter is pressed with quite considerable force, e.g. 50 N, onto the held object and thereby fixes the latter on the bearing element. As a result of the relatively inelastic pressing of the rotary wheel 6 onto the pressure plate 5, the force F2 is substantially greater than F1, preferably about 10 to 100 times greater than F1, depending on the user behaviour.

The threaded pin has a lower external thread 16, which engages with the internal thread in an opening of the bearing element 4, and has an upper external thread 17, which engages with the internal thread in a recess of the rotary wheel 6.

In the second arrangement of the fastening mechanism, a normal force FN2 is exerted parallel to the axis F, which force can be e.g. 100 N in this angle position. This normal force is the clamping force for clamping the object 2 between pressure plate 5 and bearing element 4 and holding it with the force F2, which corresponds to the effected static friction force. At this second force F2, the object cannot be moved in relation to the bearing element by the user. In the first arrangement, by contrast, the object is secured on the bearing element with a force fit in the axis-parallel position by a first force, in such a way that it can be moved in the axis-parallel position by a hand of a user.

In the first arrangement of the fastening mechanism (not shown), the object is held in the axis-parallel position on the bearing element in such a way that it is still movable by the user, e.g. at a force F1=0.5 N. The rotary wheel has then been moved further away from the bearing element by manual rotation starting from the position in FIG. 1, such that the lower face 13 of the rotary wheel then no longer presses on the pressure plate 5 in addition to the compression spring 8, and instead only the compression spring 8 presses with a force F1 on the pressure plate 5. The sum of F1 and F2 is reliably set by the user via the rotation angle of the rotary wheel 6. However, by virtue of the features of the holding device according to the invention, the forces F1 and F2 can be kept relatively low, such that comfortable operation of the holding device is permitted.

The fastening mechanism is designed as a quick-action clamping mechanism. A rotation of the rotary wheel 6 of α1=5° to α1=90° is sufficient for changing between the first arrangement and second arrangement. In this way, the change can be made quickly by hand, in particular without re-gripping.

The bearing element 4 is shaped in such a way that the cylindrical object 2, seen in cross section to the longitudinal axis thereof, or to the bearing axis A in FIG. 1, is unambiguously secured in position by the two contact points 21 and 22 with the bearing element 4, and by the third contact point 23 with the pressure plate, in all radial directions with respect to its longitudinal axis, or to the bearing axis A. In the first arrangement of the fastening mechanism, in which the force F1 acts, the object is movable in the axial direction parallel to the bearing axis A, and is rotatable within its bearing about the bearing axis A (see FIG. 3). A capillary connected to the capillary holder 2, and extending parallel to the longitudinal axis A, can therefore be rotated manually. In this way, it is possible to change the radial distance of the tip of the capillary, which has the capillary opening, in relation to the axis A. This is because the capillary tips are often not perfectly rotationally symmetrical with respect to the longitudinal axis of the capillaries. Many capillary types even have a curved tip with an end which is inclined from the longitudinal axis of the capillary and of which the direction can be changed by rotating the capillary about the longitudinal axis thereof. Therefore, as a result of this possibility of rotation about the axis A, an additional positioning possibility can be achieved for the capillary.

As in the example shown, the bearing element is preferably designed for partially form-fit connection of the object to the holding device. In the present case, the bearing element 4 is claw-shaped, since it holds the object 2, by means of a claw portion 24 and a support portion 26, with a form fit in the insert groove 25 formed by means of these portions, wherein the claw portion, seen in cross section with respect to the bearing axis A, forms the first contact point 21 and the support portion 26 forms the second contact point. The object is precisely positioned in the insert groove 25 and held securely in position by means of pressure plate 5, both in the first arrangement and also in the second arrangement of the fastening mechanism.

Moreover, the arrangement of the holding device is U-shaped or also claw-shaped, relative to the bearing portion 24, 25 and 26 of the bearing element 4 and the portion of the pressure plate 5 that supports the object 2. By virtue of this U shape, the holding device is designed such that, at least in a third arrangement of the fastening mechanism in which the object 2 can be inserted and can be removed when the distance of the pressure plate from the bearing element is sufficiently enlarged, the object can be inserted into and removed from the holding device by a movement directed perpendicularly with respect to the bearing axis A. In the present case, in the first arrangement this distance and the force F1 are such that the object is removable. This permits comfortable operation of the holding device, particularly also when it is secured, on the side of the support element 3 directed away from the bearing element 4, to a mounting mechanism for securing on a laboratory object, e.g. a microscope. The bearing element and also the object are preferably made from a non-elastic material or have such a material, preferably a metal, e.g. aluminium or steel. Through the positioning by means of an insert groove made of non-elastic material, an acoustic signal is generated, namely a click, when the object inserted by the user and made of such a material is pressed by means of the spring force of the spring mechanism into the clearly defined bearing position formed by the insert groove. This acoustic feedback likewise permits comfortable operation of the holding device.

Figure 4:
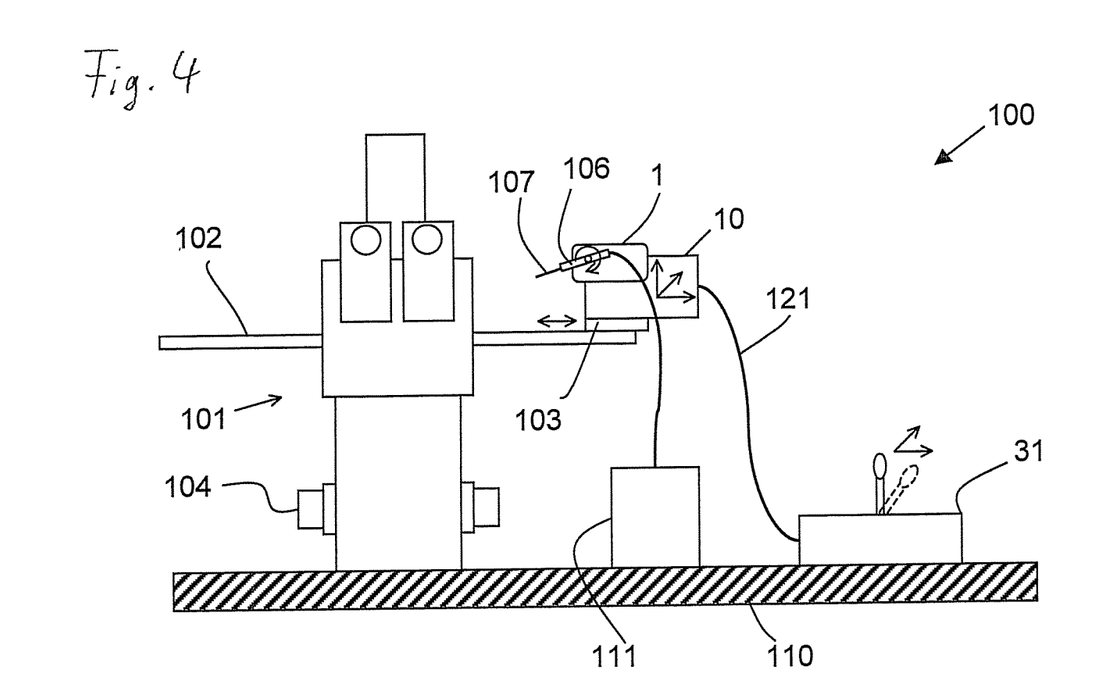
FIG. 4 shows a cell-biology workstation 100, which has various appliances and the holding device from FIGS. 1 to 3.

FIG. 4 shows a cell-biology workstation 100 having various appliances and the holding device 1. The workstation comprises a microscope 101, the piezoelectric microactuator 106 designed as capillary holder 106 with its electrical control system 111, a micropositioning mechanism 10, 31, which has the operating device 31 with joystick and the movement mechanism 10 connected thereto by a cable mechanism 121, on which movement mechanism 10 the holding device 1 for holding the object is movably mounted and is movable with great precision by the drive of the movement mechanism. The object here is a capillary holder 106 with an exchangeable capillary 107. The drive of the movement mechanism 10 has three stepper motors (not shown) by which the holding device 1 is movable along the three axes x', y', z' of a Cartesian system of coordinates, controlled by the output signal of the operating device 31 as a function of the change of position x, y, z effected by the user. The operating device controls the movement in the directions of the x-y plane by means of joystick deflection. Control is also possible particularly in the z direction, via a rotary wheel of the joystick lever head. The workstation can have further appliances, e.g. a micropump device for pumping liquids in the capillary, a second joystick mechanism, etc. The appliances are generally arranged on a laboratory bench 110. An optional pedal control device can be arranged under the bench.

In a typical application, e.g. the performance of ICSI, the user of this workstation places a Petri dish for example with a cell on the work plate 102 of the here inverted microscope 101, then brings the manually movable movement device 10 via a carriage 103 to a location near the Petri dish, then manually moves the capillary holder 106 with capillary 107 relatively quickly in the direction of the Petri dish, in particular until the capillary 107 submerges in the nutrient medium contained in the Petri dish. It is of great advantage here that the capillary holder, in the first arrangement of the holding device, is held on the bearing element with a relatively low first force, the capillary holder being able to be adjusted with one hand by the user. The first force is strong enough to hold the capillary holder against the force of gravity when the user lets go of the capillary holder. With suitable resolution of the microscope, the manual positioning can be performed relatively precisely. Under the microscope, the user now observes the capillary moving in the direction of the cell. By virtue of the precise axial mounting of the capillary holder on the bearing element, the translation movement of the capillary holder always takes place with precision along the axis A. The user can in particular rotate the capillary holder so as to attain another orientation of the capillary tip relative to the axis A, in so far as the capillary tip is not arranged centrally on the axis A of the capillary. This is often the case, for production reasons, particularly in the case of capillaries with a curved tip. In the desired end position of the manual method, the user can reliably fix the capillary holder with one hand by a simple rotation movement of the rotary knob 6 through 180°, such that the capillary holder is held by a second force that is greater than the first force and permits safe and oscillation-free positioning of the capillary and manipulation of the cell.

The manual movement of the capillary holder is followed by the motor-controlled, precise positioning by means of joystick and movement mechanism. With one hand, the user turns the focussing wheel 104 of the microscope to adjust the optical focus between capillary tip and cell, in order to observe the distance of the capillary tip from the target point on the cell. In proximity to the cell, precision control in the range here of 50 nm to 15 μm is achieved by slight excursion of the joystick. In this application, it is advantageous that the operation of the workstation and of its appliances, in particular of the holding device 1, takes place using one hand and in a manner that is intuitive and comfortable.

The invention claimed is:

1. A holding device (1) for holding an object (2) extending along an axis, the object being a capillary holder (2) of a micromanipulator,
with a main body (3, 4) having
a support element (3) and a bearing element (4) which runs parallel to a bearing axis and on which the object (2) can be mounted in an axis-parallel position in which the axis of the object and the bearing axis (A) of the bearing element run parallel,
a fastening mechanism (4, 5, 6, 7, 8) which can be optionally set by the user in at least a first or a second arrangement and is designed in such a way that,
in the first arrangement of the fastening mechanism, the object (2) is secured with a force fit on the bearing element (4) in the axis-parallel position, such that it is held by a first force (F1) directed parallel to the axis and, when said first force is overcome, the object is movable by a hand of a user in the axis-parallel position, and in such a way that,
in the second arrangement of the fastening mechanism, the object (2) is fixed on the bearing element, in the axis-parallel position (A), against movement in the direction parallel to the axis by a second force (F2), which is greater than the first force (F1),
wherein the holding device (1) is designed such that the object (2), at least in a third arrangement of the fastening mechanism, can be inserted into the holding device (1) by a movement directed perpendicularly with respect to the bearing axis (A),
wherein the fastening mechanism has an actuating element being a rotary knob, with which the user can optionally set the first or the second arrangement of the fastening mechanism,
and the fastening mechanism has a pressure element (5) which is mounted movably on the bearing element (4), wherein, in the first and second arrangements of the fastening mechanism, the object is pressed against the bearing element (4) by the pressure element (5), as a result of which the force-fit fastening of the fastening mechanism is effected, and
wherein the fastening mechanism has a spring mechanism (8), including a compression spring, by which the pressure element (5), in the first arrangement, is pressed resiliently against the object (2), such that the pressure element (5) remains deflectable counter to the action of the spring force at least in a direction perpendicular to the axis,
the rotary knob being rotatable about a rotary-knob axis (F), wherein, in the first and second arrangement, the compression spring is compressed on the pressure element in the direction of the rotary-knob axis (F) by abutting on the pressure element and on the rotary knob,
and wherein the fastening mechanism is designed such that the pressure element (5), in the second arrangement, is pressed non-resiliently against the object, such that the pressure element is not deflectable counter to the direction of the spring force, by providing that
the rotary knob has a contact section, which, in the second arrangement of the fastening mechanism, additionally contacts the pressure element and presses against the pressure element such that, by means of this contact section and the spring mechanism, the rotary knob transfers the second force (F2) to the pressure element, which fixes the object on the bearing element, the bearing element is secured on the support element so as to be rotatable by a rotation angle about an axis (R), which is parallel to the rotary-knob axis (F) and which runs through the bearing element and the support element, wherein the support element has a fixing mechanism (14, 15) such that the bearing element rotated with respect to the support element can be fixed on the support element at the desired rotation angle, wherein the fixing mechanism has an actuating element (15), with which the user can operate the fixing mechanism.

2. A holding device according to claim 1, wherein the bearing element has an axis-parallel insert groove into which the object can be placed.

3. A holding device according to claim 1, wherein the pressure element is a plate-shaped pressure element and wherein said plate-shaped pressure element has two opposite faces (5', 5"), wherein, in the first and second arrangements, a contact area (23) of one of said faces (5') of said plate-shaped pressure element can be brought into contact with the object (2), as a result of which the latter can be pressed against an insert groove (25).

4. A holding device according to claim 1, wherein the rotary knob (6) is mounted on the bearing element (4) and serves as an abutment for the spring mechanism (8) by which, in the first arrangement of the fastening mechanism, a first force can be transferred to the pressure element and therefore to the object, wherein the object (2), in the second arrangement of the fastening mechanism, can be secured with a force fit on the bearing element (4) in the axis-parallel position (A) by a second force directed parallel to the axis, which second force is greater than the first force and by which the object can be fixed on the bearing element, such that an object mounted in the axis-parallel position is not movable parallel to the axis by a hand of a user, since a contact section (13) of the rotary knob (6) contacts the pressure element (5) and presses against the pressure element such that, by means of this contact section, a force perpendicular to the axis is transferred by the rotary knob to the pressure element and this second force is generated.

5. A micromanipulator arrangement comprising the holding device according to claim 1 and a securing device for securing the holding device on a laboratory object.

* * * * *